United States Patent [19]

Kouwenhoven et al.

[11] 4,238,318

[45] Dec. 9, 1980

[54] CRYSTALLINE SILICATES AND HYDROCARBON-CONVERSION PROCESSES EMPLOYING SAME

[75] Inventors: Herman W. Kouwenhoven; Willem H. J. Stork, both of Amsterdam, Netherlands

[73] Assignee: Shell Oil Company, Houston, Tex.

[21] Appl. No.: 83,497

[22] Filed: Oct. 10, 1979

Related U.S. Application Data

[62] Division of Ser. No. 858,136, Dec. 7, 1977, Pat. No. 4,208,305.

[30] Foreign Application Priority Data

Dec. 16, 1976 [NL] Netherlands ......................... 7613957

[51] Int. Cl.$^3$ .................... C10G 11/05; C10G 35/095; C10G 47/18
[52] U.S. Cl. .................................... 208/120; 208/124; 208/111; 208/137; 208/950; 423/326; 585/408; 585/409; 585/415; 585/417; 585/418
[58] Field of Search ............................... 585/408–409, 585/415, 417, 418; 208/950, 111, 120

[56] References Cited

U.S. PATENT DOCUMENTS

| | | | |
|---|---|---|---|
| 3,702,886 | 11/1972 | Argauer et al. | 208/111 X |
| 3,941,871 | 3/1976 | Dwyer et al. | 252/454 |
| 4,039,600 | 8/1977 | Chang | 585/408 |
| 4,061,724 | 12/1977 | Grose et al. | 423/339 X |

FOREIGN PATENT DOCUMENTS

| | | | |
|---|---|---|---|
| 2017807 | 11/1970 | Fed. Rep. of Germany | 423/328 |
| 1264545 | 2/1972 | United Kingdom | 423/328 |

OTHER PUBLICATIONS

Chem. Abstracts 74 16102y (1971) for Ger. 2,017,807.
Chem. Abstracts 76 129676y (1972) for Brit. 1,264,545.

*Primary Examiner*—Delbert E. Gantz
*Assistant Examiner*—G. E. Schmitkons
*Attorney, Agent, or Firm*—Ronald R. Reper

[57] ABSTRACT

Novel crystalline silicates which in dehydrated form have the composition in terms of moles of the oxides: $(1.0\pm 0.3)(R)_{2/n}O \cdot [aFe_2O_3 \cdot bAl_2O_3 \cdot cGa_2O_3 \cdot y(dSiO_2 \cdot eGeO_2)]$, wherein R is one or more mono- or bivalent cations and a, b, c, d, e, y and n are as defined hereinafter are disclosed. The thermally stable silicates are suitably employed as extracting agents, drying agents, ion exchange agents, catalysts and catalyst carriers.

8 Claims, No Drawings

CRYSTALLINE SILICATES AND HYDROCARBON-CONVERSION PROCESSES EMPLOYING SAME

This is a division, of application Ser. No. 858,136, filed Dec. 7, 1977 (now U.S. Pat. No. 4,208,305).

BACKGROUND OF THE INVENTION

The invention relates to novel crystalline silicates and to a process for their preparation. The invention further relates to the use of these silicates, inter alia, as adsorbing and extracting agents, as drying agents, as ion exchangers and as catalysts or catalyst carriers for various catalytic processes, in particular for the catalytic preparation of aromatic hydrocarbons.

The crystal structure of the silicates according to the invention has interstices of molecular dimensions, which are usually filled with hydration water. After at least partial dehydration the silicates can be used as efficient adsorbing agents, the adsorbed molecules being retained in the interstices. These interstices are accessible via openings in the crystal structure. Depending on the cross-sectional area of these openings the dimensions and the shape of the molecules, which can be adsorbed, are restricted. This enables certain molecules to be separated from mixtures on the basis of molecular dimensions, certain molecules being adsorbed by the silicates whereas others are rejected. Materials having this property are usually referred to as molecular sieves. This property of the silicates according to the invention may be utilized when they are used as catalysts or catalyst carriers in selectively carrying out processes in which either from a mixture of compounds differing in structure only the compounds having a specific structure are converted, or from a compound a compound only compounds having a specific structure are formed, as a result of the fact that only compounds having that specific structure can, respectively, penetrate into or leave the silicates.

The silicates according to the invention are characterized as a class of compounds by their thermal stability, their adsorption behavior and their overall composition. The crystallinity of the various compounds follows from the fact that they all show a clear X-ray powder diffraction pattern.

SUMMARY OF THE INVENTION

The invention provides novel silicates which in the dehydrated form, have the following overall composition, in terms of moles of the oxides:

$(1.0 \pm 0.3)(R)_{2/n}O \cdot [aFe_2O_3 \cdot bAl_2O_3 \cdot cGa_2O_3] \cdot y(dSiO_2 \cdot e(GeO_2))$, where R = one or more monovalent or bivalent cations;
$a \geq 0.1$;
$b \geq 0$;
$c \geq 0$;
$a + b + c = 1$;
$y \geq 10$;
$d \geq 0.1$;
$e \geq 0$;
$d + e = 1$; and
n = the valency of R.

The silicates according to the invention are thermally stable up to temperatures above 600° C. and—after dehydration in vacuum at 400° C.—are capable of adsorbing more than 3%w water at 25° C. and saturated water vapor pressure. In this patent application a silicate is said to be thermally stable up to temperatures above t° C. if heating of the silicate to the temperature of t° C. does not substantially affect the X-ray powder diffraction pattern of the silicate.

The present patent application therefore relates to novel crystalline silicates with the above-mentioned overall composition, thermal stability and adsorption behavior.

The invention further provides a process for preparation of said crystalline silicates which comprises:
maintaining at an elevated temperature until the silicate is formed, a reaction mixture which comprises: at least one compound of an alkali or alkaline earth metal ($R_1$), at least one compound containing a monovalent or a bivalent organic cation ($R_2$) or from which such a cation is formed "in situ" during preparation of the silicate, at least one silicon compound, at least one iron compound, and optionally at least one compound of aluminum, gallium and/or germanium in which mixture the various compounds are present in the following molar ratio, expressed in moles of the oxides:

$(R_1)_{2/p}O : (R_2)_{2/q}O \geq 10$ and preferably 0.05–5,
$(R_2)_{2/q}O : (SiO_2 + GeO_2) = 0.01 – 1$ and preferably 0.05–1,
and
$(SiO_2 + GeO_2) : (Fe_2O_3 + Al_2O_3 + Ga_2O_3) \geq 10$ and preferably 10–600, where p and q are the respective valences of $R_1$ and $R_2$, and then separating the crystals of silicate from the mother liquor, i.e. the remainder of the reaction mixture. The invention further provides a process for the conversion of hydrocarbons which comprises contacting said hydrocarbons with a crystalline silicate according to the invention, under hydrocarbon converting conditions.

DESCRIPTION OF PREFERRED EMBODIMENTS

The crystalline silicates according to the invention consist structurally of a three-dimensional network of $SiO_4$—, $FeO_4$— and, optionally, $AlO_4$—, $GaO_4$— and $GeO_4$—tetrahedrons, which are interlinked by common oxygen atoms. The negative electrovalency of the tetrahedrons containing iron and, optionally, aluminum and gallium is in equilibrium because of occlusion in the crystal of monovalent and/or bivalent cations. Unlike the silicon, iron, and optionally, aluminum, gallium and germanium atoms present which are non-exchangeable, these cations can, at least partly, be replaced by others when suitable exchange methods are used. The silicates according to the invention are therefore suitable for use as ion exchangers. Apart from iron, and optionally, aluminum and gallium present in the above-mentioned $FeO_4$—, $AlO_4$— and $GaO_4$—tetrahedrons, the silicates according to the invention may also contain minor quantities of iron, aluminum and/or gallium, which metals do not form part of the crystal structure of the silicates. This contaminant iron which may occur e.g. in the form of precipitated hydroxide in and/or between the silicate crystals does not contribute to the above-mentioned negative electrovalency.

Preference is given to silicates not containing gallium and germanium, in other words: silicates of which c and e in the abovementioned overall composition are equal to 0. Further preference is given to silicas of which a in the above-mentioned overall composition is larger than 0.3 and in particular of which a is larger than 0.5. Silicates in which no aluminum occurs, in other words: silicas of which b in the above-mentioned overall composition is equal to 0, are especially preferred. With respect to y it can be remarked that silicas in which y is smaller than 600 and in particular smaller than 300, are preferred. Special preference is given to silicates according to the invention whose X-ray powder diffraction patterns show, inter alia, the reflections given in Table A.

TABLE A

| $2\theta$ | Relative intensity |
|---|---|
| 7.8–8.2 | S |
| 8.7–9.1 | M |
| 11.8–12.1 | W |
| 12.4–12.7 | W |
| 14.5–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M |

The values given in Table A have been determined according to standard methods. Radiation: Cu-Ka, wavelength: 0.15418 nm. The letters in Table A used to indicate the relative intensities have the following meanings: VS=very strong; S=strong; M=moderate; W=weak; $\theta$=angle according to Bragg's law.

The complete X-ray powder diffraction pattern of a silicate according to the invention which is particularly preferred is given in Table B. (Ratiation: Cu-Ka, wavelength: 0.15418 nm).

TABLE B

| $2\theta$ | Relative intensity (100. $I/I_o$) | description of the reflection |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*$I_o$ = intensity of the strongest separated reflection occurring in the pattern.

The letters in Table B used to describe the reflections have the following meanings: SP=sharp; SR=shoulder; NL=normal; BD=broad; $\theta$=angle according to Bragg's law.

Silicates according to the invention are prepared from an aqueous mixture containing the following compounds: one or more compounds containing a monovalent or bivalent organic cation ($R_2$) or from which such a cation is formed during the preparation of the silicate, one or more silicon compounds, one or more iron compounds and, optionally, one or more compounds of an alkali or alkaline-earth metal ($R_1$) and one or more aluminum-, gallium- and/or germanium compounds. The preparation is effected by maintaining the mixture, preferably while stirring, at elevated temperature until the silicate has been formed, followed by separation of the silicate crystals from the mother liquor. In the aqueous starting mixture from which the silicates according to the invention are prepared the various compounds must be present in the following molar ratios, expressed in moles of the oxides:

($R_1)_{2/p}O:(R_2)_{2/q}O \leq 10$
($R_2)_{2/q}O:(SiO_2+GeO_2)=0.01–1$, and
$(SiO_2+GeO_2):(Fe_2O_3+Al_2O_3+Ga_2O_3) \geq 10$; p and q are the respective valencies of $R_1$ and $R_2$.

In addition to the novel silicates the present patent application also relates to a process for the preparation of the novel silicates starting from an aqueous mixture having the above-mentioned composition, by maintaining this mixture at elevated temperature until the silicate has been formed, followed by isolation of the silicate from the mother liquor. In the aqueous starting mixture from which the silicates according to the invention are prepared, the various compounds are preferably present in the following molar ratios, expressed in moles of the oxides:

($R_1)_{2/p}O:(R_2)_{2/q}O=0.5–5$
($R_2)_{2/q}O:(SiO_2+GeO_2)=0.05–1$
$(SiO_2+GeO_2):(Fe_2O_3+Al_2O_3+Ga_2O_3)=10–600$.

The preparation of the silicates according to the invention may be effected either at atmospheric pressure or at elevated pressure. When reaction temperatures exceeding the boiling point of the mixture are used, it is preferred to work in an autoclave under autogenous pressure. The silicates are preferably prepared by maintaining the mixture for at least four hours at a temperature between 90° and 300° C. and in particular at a temperature between 125° and 175° C. After formation of the silicates the crystals are separated from the mother liquor, e.g. by filtration, decanting or centrifuging. The crystal mass is then washed with water and finally dried at a temperature between 100° and 200° C.

If the silicates according to the invention are obtained in the form of products of colloidal size, further processing thereof may be facilitated by removing the excess siliceous components and soluble salts from the aqueous suspension of said colloidal silicate in the mother liquor remaining after crystallization of said silicate, either by contact with an exchange resin selected from the group consisting of anionic, cationic and mixtures of anionic and cationic resins, said resins being in a particle form of a size large enough for easy separation from the suspension, or by contacting the aqueous suspension of said silicate with a semi-permeable membrane which permits passage of excess silicate and soluble salts, the other side of which membrane is in contact with an aqueous treating solution, said treating solution being of lower salt concentration than said aqueous colloidal silicate suspension. The suspension of the silicate may e.g. alternatively be treated with cationic Dowex-50 (H+ form) and with anionic Dowex-1 (OH− form), or the suspension of the silicate may be contacted via semi-permeable membrane with demineralized water.

Silica pore obstructure, which may occur in the preparation of the silicates according to the invention, may be reduced by incorporating an alkali metal salt containing a monovalent anion in the base mixture from which the silicate is prepared. Examples of suitable salts are $NaCl$, $KBr$, $NaNO_3$ and $LiCl$.

The quaternary ammonium compounds which are as a rule employed in the base mixture from which the silicates according to the invention are prepared may be replaced by a mixture of at least one compound of the formula $R_1R_2R_3N$ and at least one compound of the formula $R_4X$, in which $R_1$, $R_2$ and $R_3$ are hydrocarbon radicals or hydrogen, $R_4$ is a hydrocarbon radical and $X$ is an electronegative group. Examples of such mixtures are those comprising, $(C_2H_5)_3N + (C_2H_5)_2SO_4$, $(C_4H_9)_3N + (C_2H_5)_2SO_4$, $(C_3H_7)_3N + C_3H_7)_3N + C_3H_7OH$. The quaternary ammonium compounds may also be replaced by primary amines having 2–10 carbon atoms in the molecule.

As examples of suitable compounds that may be used in the preparation of the silicates according to the invention may be mentioned: nitrates, carbonates, hydroxides and oxides of alkali and alkaline-earth metals; primary, secondary and tertiary alkylamines and quaternary alkylammonium compounds, such as bromides and hydroxides; iron oxide, iron nitrate and ammonium ferrous sulphate; aluminum hydroxide, sodium aluminate and activated aluminas, such as gamma-alumina; sodium silicate, silica gels, silicic acid, aqueous colloidal silica sols and amorphous solid silicas, such as precipitated silica sols; gallium nitrate, gallium oxide and germanium oxide. In the preparation of the silicates according to the invention preference is given to a basic mixture in which $R_1$ is present in an alkali-earth metal compound and $R_2$ in a tetraalkylammonium compound and in particular to a basic mixture in which $R_1$ is present in a sodium compound and $R_2$ in a tetrapropylammonium compound. The silicates according to the invention are as a rule prepared from an aqueous mixture containing an alkali or alkaline-earth metal. They may, however, also be prepared from aqueous mixtures in which such metals do not occur.

As was mentioned earlier the silicates according to the invention contain exchangeable cations. In the silicates obtained by heating the above-mentioned aqueous mixture these exchangeable cations are alkali and/or alkaline-earth metal ions as well as monovalent and/or bivalent organic cations. Through the use of suitable exchange methods the alkali and alkaline-earth metal ions can be replaced by other cations, such as hydrogen ions, ammonium ions or ions of the rare-earth metals. Monovalent and bivalent organic cations can very suitably be converted into hydrogen ions by calcination of the silicates.

When the silicates according to the invention contain alkali metals and when it is intended to use these silicates as catalyst or catalyst carrier, it is preferable to reduce the alkali metal content of these silicates beforehand to less than 1%w and particularly to less than 0.05%w. The reduction of the alkali metal content of the silicates may very suitably be effected by contacting them once or several times with a solution containing exchangeable cations. By treating the silicates, for instance, with a solution containing ammonium ions, $NH_4{}^+$—silicates can be prepared. By calcination of the $NH_4{}^+$—silicates are converted to the hydrogen form, i.e. $H^+$—silicates. The calcination may be carried out in such a way that at least part of the monovalent and/or bivalent organic cations present in the silicate is converted into hydrogen ions.

Silicates according to the invention possess catalytic activity and may therefore be used per se as catalysts. They may also be used as catalyst carriers for one or more catalytically active metal components. Depending on the envisaged use of the catalyst, metals that may be emplaced on the silicates according to the invention are the metals of Groups IB, IIB, VB, VIB, VIIB and VIII of the Periodic Table. In this patent application the term Periodic Table refers to the Periodic Table of Elements as included in the Handbook of Chemistry and Physics, 55th edition, p. B2. Among these metals are copper, silver, zinc, cadmium, vanadium, chromium, molybdenum, tungsten, manganese, the metals of the iron group and the metals of the platinum group. Emplacement of the metals on the silicates may be effected in any conventional way e.g. by impregnation, percolation, ion exchange and the like. To increase the activity, selectivity and/or stability of the catalysts based on the silicates according to the invention promoters such as halogen, phosphorus, boron, arsenic and antimony may be incorporated. Very suitable catalysts for many kinds of processes are catalysts comprising one of the following catalytically active metals or metal combinations on a silicate according to the invention as the carrier: nickel, copper, zinc, platinum, palladium, nickel-tungsten, cobalt-molybdenum, nickel-molybdenum, zinc-palladium, zinc-copper and zinc-rhenium.

When silicates according to the invention are used for catalytic purposes, the material should generally be available in the form of particles with a diameter of 0.5–5 mm. In the mode of preparation described hereinbefore the silicates are obtained in the form of a fine powder. The silicates may be shaped into particles of larger size, for instance by pressing. During shaping the silicate may be combined with an inorganic matrix or binder material, if desired. Examples of suitable matrix or binder materials are naturally occurring clays, such as kaolin and bentonite. Other suitable matrix or binder materials are synthetic inorganic oxides, such as alumina, silica, boria, thuria, zirconia and the like or combinations thereof, such as silica-alumina and silica-zirconia. When silicates according to the invention are combined with a matrix or binder material, any mixing ratio may in principle be used. Preference is given to a matrix or binder material which does not contain any alkali metal or whose alkali metal content is very low. For the sake of brevity catalysts consisting at least partly of a silicate according to the invention will further be referred to in this patent application as "catalysts according to the invention." Catalyst according to the invention used for hydrocarbon conversion processes show as a rule a higher stability if the silicate present therein has an ultimate particle size of 0.005–0.1 micron. Silicates of this small particle size may be obtained by using in the aqueous mixture from which the silicates are prepared a high concentration of the organic component.

Although catalysts according to the invention have very long lives, it is nevertheless desirable from time to time to carry out a regeneration. For many hydrocarbon conversion processes this can very simply be done by burning off the catalyst.

Catalysts according to the invention may be used successfully in the following conversion processes:
1. Catalytic cracking of heavy hydrocarbon mixtures for the preparation of light hydrocarbon oil distillates;
2. Preparation of isoparaffins by isomerization of n-paraffins;
3. Hydrodesulfurization of hydrocarbon oil distillates;
4. Conversion of naphthenes into aromatics;
5. Polymerization of olefins for the preparation of polyolefins.

Silicates according to the invention are further suitable for application in the following processes:
1. Hydrocracking of heavy hydrocarbon oils for the preparation of light hydrocarbon oil distillates, such as the conversion of gas oil into gasoline.

For this purpose the heavy hydrocarbon oil may be contacted under hydrocracking conditions with a catalyst according to the invention comprising
(a) a zeolite with a pore size larger than 7 Å, (b) a silicate according to the invention and (c) one or more metal components with hydrogenating-/dehydrogenating activity combined with at least one of the materials (a) and (b). A very suitable catalyst for the preparation of gasoline by hydrocracking of gas oil is a catalyst comprising a mixture of $Ni/W/SiO_2$—$Al_2O_3$ with a Ni-W-impregnated mixture of HCS and rare-earth-exchange zeolite X.

2. Hydrocracking of heavy hydrocarbon oils for the preparation of high-viscosity-index lubricating oils. For this purpose the heavy hydrocarbon oil may be contacted under hydrocracking conditions with a catalyst according to the invention comprising (a) an amorphous or crystalline wide pore cracking catalyst, (b) a silicate according to the invention and (c) one or more metal components with hydrogenating/dehydrogenating activity. A very suitable catalyst for the preparation of a low pour point high VI lubricating oil by hydrocracking of a heavy hydrocarbon oil is a catalyst comprising a mixture of Ni-W-impregnated $SiO_2/ZrO_2$/clay catalyst with Zn/HCS. Very suitable catalysts for the preparation of lubricating oil from foots oil are Zn/HCS and Ni/HCS.

3. Improving the light and oxidation stability of lubricating oils prepared conventionally or by hydrocracking, by contacting the oils at elevated temperature with a silicate according to the invention. Improved results may be obtained by performing the contacting in the presence of a small amount of added n-paraffin, sulphur or sulphur compounds.

4. Upgrading of cat cracked gasoline by contacting the gasoline in the presence or in the absence of hydrogen with a catalyst according to the invention. The process may e.g. be carried out by splitting the cat cracked gasoline into a $C_6^-$ overhead fraction and a $C_7^+$ bottom fraction, contacting only the $C_7^+$ bottom fraction at elevated temperature and pressure with a catalyst according to the invention and blending of the treated $C_7^+$ fraction with the non-treated $C_6^-$ fraction. A very suitable cat cracked gasoline for upgrading over a catalyst according to the invention is a gasoline prepared in a cat cracking process carried out in such a way that a $C_6^+$ gasoline containing less than 15%w olefins is obtained. This $C_6^+$ gasoline may very suitably be upgraded in the absence of hydrogen over HCS or in the presence of hydrogen over Ni/HCS.

5. Preparation of olefins from alcohols and/or ethers having not more than 4 carbon atoms per alkyl group by contacting them with a catalyst according to the invention at such a low severity that the catalyst shows only a small activity for aromatization. By contacting methanol or dimethylether with HCS a product can be obtained substantially consisting of $C_2$-$C_4$ olefins.

6. Preparation of olefinic gasoline containing less than 20%w of aromatics by contacting $C_2$-$C_5$ olefins or mixtures thereof with $C_1$-$C_5$ paraffins at elevated temperature with a silicate according to the invention of which the alpha-value (as defined in U.S. Pat. No. 3,960,978) has been decreased to 0.1-120. A decrease of the alpha-value of the silicates according to the invention may be obtained by using them first in a high temperature aromatization process or by steaming them. Excellent gasoline may be obtained in this process by contacting propene or a $C_2$-$C_3$ paraffins/olefins mixtures with Zn/HCS, Cr/HCS or Ni/HCS.

7. Upgrading of naptha by shape selective hydrocracking by contacting the naphtha at elevated temperature and pressure and in the presence of hydrogen with a catalyst according to the invention, e.g. Ni/HCS.

8. Catalytic hydrodewaxing of hydrocarbon oils by contacting the oils at elevated temperature and pressure and in the presence of hydrogen with a catalyst according to the invention. In this way lubricating oil and shale oil may be dewaxed by contacting them with e.g. Zn/HCS. The catalytic hydrodewaxing of lubricating oil in this way may be carried out as the second step of a two-step dewaxing process in which the wax content of the lubricating oil is decreased in a first step by solvent dewaxing. The catalytic hydrodewaxing process according to the invention may also very suitably be applied for lowing the freezing point of jet fuel.

9. Separation of hydrocarbon mixtures, especially the separation of p-xylene from a mixture of isomeric xylenes by contacting the mixture with a silicate according to the invention. Examples of mixtures of hydrocarbons which may be separated with the aid of a silicate according to the invention are 2,2-dimethyl butane/2-methyl pentane; iso-octane/3-methyl pentane; iso-octane/2,5-dimethyl cyclohexane/methyl cyclohexane; o-diethyl benzene/p-diethyl benzene; 2-ethyl toluene/4-ethyl toluene. For the separation of p-xylene from a mixture of isomeric xylenes a silicate according to the invention which has been modified by reaction with a silane carrying an organic radical, such as octadecyl trichlorosilane, is preferred.

10. Transalkylation of alkyl-substituted aromatics by contacting them under transalkylation conditions with a catalyst according to the invention. This process may be applied e.g. for the preparation of ethylbenzene from a mixture of benzene and diethyl benzene.

11. Alkylation of aromatics by contacting them together with an alkylation agent under alkylation conditions with a catalyst according to the invention. The process may be applied e.g. for the preparation of ethyl benzene from benzene and ethene.

12. Alkylation of olefins for the preparation of higher olefins by contacting olefins such as ethene, propene, butene-2 or isobutene and an alkylation agent such as dimethyl ether under alkylation conditions with a catalyst according to the invention.

13. Conversion of ethylbenzene and aliphatic hydrocarbons present in a xylene mixture by contacting the mixture at elevated temperature and pressure and in the presence of hydrogen with a catalyst according to the invention such as Ni/HCS. In this way the mixture becomes more suitable as feed for an isomerization plant for the preparation of p-xylene. The hydrotreatment makes the usual aromatic extraction and ethyl benzene fractionation of the crude mixture superfluous.

Catalysts according to the invention are eminently suitable for application in the following processes:

1. Catalytic dewaxing of gas oil to improve the cloud point thereof. The process is carried out by contacting the gas oil at elevated temperature in the gaseous or liquid phase and either in the presence or in the absence of hydrogen with a catalyst according to the invention.

The catalytic dewaxing of gas oil may very suitably be combined with a catalytic hydrodesulphurization and hydrodenitrogenation of the dewaxed gas oil carried out in a second stage over a Co/Mo/Al$_2$O$_3$ catalyst. A very suitable catalyst for the catalytic hydrodewaxing of gas oil is a catalyst according to the invention comprising at least one Group VIII noble metal, such as Zn/Pd/HCS. Compared with other catalysts according to the invention such as Ni/HCS, Zn/Pd/HCS shows a higher activity and stability in the hydrodewaxing of gas oil. If the catalytic dewaxing of gas oil is carried out in the presence of hydrogen, the hydrogen consumption may be decreased either by application of a catalyst according to the invention comprising a silicate with a crystal size of about 0.05 micron in combination with a low pressure of by dividing the gas oil into a portion with a pour point below 1° C. and a rest, hydrodewaxing only the rest and blending the hydrowaxed portion with the non-treated portion.

2. Preparation of p-xylene by isomerization of other C$_8$-aromatics. The process is carried out by contacting the C$_8$-aromatics under isomerization conditions either in the liquid phase or in the gase phase and in the presence of hydrogen with a catalyst according to the invention (e.g. Ni/HCS).

3. Preparation of p-xylene by methylation of toluene. The process is carried out by contacting toluene and a methylation agent such as methanol, methyl chloride, methyl bromide, dimethyl ether or dimethyl sulphide under methylation conditions with a catalyst according to the invention. For this application it is preferred to use silicate catalyst particles of an average crystal size greater than 0.5 micron, which catalyst particles have been surface-deactivated by reaction with a nitrogen or silicon compound of a size sufficiently large as to be unable to penetrate the pore structure of the silicate. Examples of suitable silicon and nitrogen compounds are dimethyl dichlorosilane and phenyl carbazole. Modification of the surface of a catalyst according to the invention for the preparation of p-xylene by methylation of toluene can also very suitably be performed by contacting the catalyst with a polymer made up of meta-carbonate units connected by siloxane units and of a size sufficiently large as to be unable to penetrate the silicate pore structure. Another way of modifying the surface of a catalyst according to the invention for the preparation of p-xylene by methylation of toluene is by means of a treatment in which a coating of between 15 and 75% of coke is deposited thereon. In the preparation of p-xylene by methylation of toluene in the presence of a catalyst according to the invention it is preferred to use a catalyst comprising a silicate of which the alpha-value (determined as described in Journal of Catalysis, Vol. IV, No. 4, August 1965, pages 527–529) has been decreased to a value below 500 by a steam treatment. To decrease the formation of m-xylene it is preferred to use a silicate wherein at least 0.5%w of P, As or Sb has been incorporated. The methylation is preferably carried out at a temperature between 575° and 700° C. A very suitable catalyst for the preparation of p-xylene by methylation of toluene is a catalyst according to the invention which has been modified by the addition thereto of phosphorus in an amount of at least 0.5%w and activated by vapor phase treatment with a mixture of methanol and water at a temperature between 400° and 650° C. for a period of at least 1 hour. Other very suitable catalysts for the preparation of p-xylene by methylation of toluene are the following catalysts according to the invention:

(a) a catalyst containing at least 0.2%w boron;
   (b) a catalyst containing at least 0.5%w magnesium;
   (c) a catalyst containing an oxide of antimony.

4. Preparation of p-xylene by disproportionation of toluene under disproportionation conditions with a catalyst according to the invention. Very suitable catalysts for this purpose are the following catalysts according to the invention:

(a) a catalyst containing at least 0.5%w phosphorus;
   (b) a catalyst containing an oxide of antimony;
   (c) a catalyst containing at least 0.5%w magnesium;
   (d) a catalyst containing at least 0.2%w boron;
   (e) a catalyst containing oxides of phosphorus and of magnesium.

Although catalysts according to the invention may be used successfully for each of the above-mentioned processes, yet the great importance of these catalysts lies in another field. For, it has been found that these catalysts are pre-eminently suitable for the preparation of aromatic compounds from acyclic organic compounds. As starting materials for this aromatics preparation many classes of organic compounds are eligible such as alcohols, ethers, olefins, paraffins, aldehydes, ketones and esters. It has been found that these catalysts have not only the property of forming aromatics from organic compounds having six or more carbon atoms in the molecule, such as hexadecane, but, surprisingly, are also capable of producing in high yields aromatics from organic compounds having less than six carbon atoms in the molecule, such as methanol, ethanol and propene. Another surprising property of the catalysts according to the invention is that, when used for the preparation of aromatics described hereinbefore, they yield a product in which the aromatic contain substantially at least six and at most ten carbon atoms, regardless of whether the organic compounds used as the starting material contained six or more or less than six carbon atoms. The latter property of the catalysts according to the invention is considered to be very important, since aromatic compounds having 6–10 carbon atoms in the molecule are very suitable for use as gasoline components.

In the preparation of aromatics using catalysts according to the invention the starting material may be some acyclic organic compound such as methanol or propene as well as a mixture of substantially acyclic organic compounds. The aromatization process according to the invention is very suitable for the preparation of aromatics from methanol and also for increasing the octane number of gasolines such as straightrun gasolines and gasolines obtained in hydrocracking, thermal cracking and catalytic cracking of mineral oil fractions.

The preparation of aromatic hydrocarbons from aliphatic and/or cycloaliphatic hydrocarbons is carried out by contacting the feed under aromatization conditions with a catalyst according to the invention. Examples of suitable starting materials for the preparation of aromatics are ethene, propene, butene, propane, butane, pentane, n-hexane, methyl pentane, methyl cyclopentane, Udex raffinates, straight run gasoline fractions, pyrolysis gasoline fractions and products obtained in the hydrocarbon synthesis according to Fischer-Tropsch. Examples of suitable catalysts according to the invention are HCS, Zn/HCS, Pt/HCS, Ni/HCS, Au/HCS, U/HCS and Zn/Cu/HCS. In the preparation of aromatics from olefins and paraffins the aromatics yield may be increased by incorporating oxygen or air in the feed. The yield of aromatics may also be increased by performing the process in two steps, first over a catalyst according to the invention and a zeolite with pores of 4.5–6.7 Å, e.g. a mixture of HCS and erionite. In addition to aromatics a gaseous product is formed. The propane content of this gaseous product may be increased by performing the second step of the process in the presence of hydrogen. In the preparation of aromatics from aliphatics the yield of alkylsubstituted aromatics may be increased by performing the process in two steps, e.g. first over Zn/HCS and thereafter over HCS. The formation of naphthalene and coke during the aromatization reaction may be suppressed by application of a catalyst according to the invention comprising the metal combination Zn-Re. In the preparation of aromatics from lower olefins it is preferred to first oligomerize the olefins to olefins with a higher molecular weight over a catalyst according to the invention and thereafter aromatize these higher olefins again over a catalyst according to the invention. In the first step of the prcess considerably milder conditions are applied than in the second aromatizing step. In this way propene may e.g. by converted into a mixture of aromatics by contacting it is a first step at relatively low temperature and high space velocity with Ni/HCS and contacting the product thus obtained in a second step at relatively high temperature and low space velocity with Ni/HCS and contacting the product thus obtained in a second step at relatively high temperature and low space velocity with Zn/HCS. An attractive embodiment of the aromatization process is one in which the product of the aromatization is split up into a gaseous and a liquid phase, in which the gaseous phase is subjected to dehydrogenating cracking to increase the olefinic content and in which the olefin-rich fraction is recirculated to the reactor in which the aromatization takes place. If the aromatization reaction is used for the upgrading of naphtha, the production of $C_3$ and $C_4$ gas may be increased and the production of $C_1$ and $C_2$ gas decreased by application of a catalyst according to the invention having aluminum incorporated in the interstices of the silicate crystal. If the aromatization reaction is used for the upgrading of naphtha, a higher liquid yield may be obtained by application of a catalyst according to the invention comprising Zn or Cd and having a modified activity equivalent to the incorporation of 0.1–3%w of an element of Group Ia (Na, K or Li) or Va (P, Sb or As). Instead of incoporating one of these elements in the silicate, the modification may also be performed by steaming of the silicate.

In addition to aliphatic and cycloaliphatic hydrocarbons, hydrocarbons containing a hetero atom such as an oxygen, halogen, sulphur or nitrogen atom, may be used as feed for the aromatization process according to the invention. Examples of suitable compounds of this type are: methanol, ethanol, isopropanol, 2-ethyl hexanol, mixed oxo alcohols, mixed pentanols, methanol/propene mixtures, methyl mercaptan, dimethyl ether, tri n-butyl amine, methyl formate, acetic acid, acetone, propion aldehyde, cyclo pentanone, n-butyl formate, n-propyl acetate and caprioc acid. The aromatization process according to the invention may also be applied for the preparation of an aromatic gasoline from carbohydrates into a mixture of water and alcohols and therafter converting this mixture into an aromatic gasoline over a catalyst according to the invention.

The aromatization process according to the invention is pre-eminently suitable for application to hydrocarbons and/or oxygen-containing hydrocarbons obtained in the conversion of a mixture of carbon monoxide and hydrogen. The conversion of a mixture of carbon monoxide and hydrogen into an aromatic hydrocarbon mixture may be carried out in two steps. In the process a mixture of carbon monoxide and hydrogen is contacted in the first step with a catalyst comprising one or more metal components with catalytic activity for the conversion of a $H_2/CO$ mixture into hydrocarbons and/or oxygen-containing hydrocarbons. In the second step the product thus obtained is converted into an aromatic hydrocarbon mixture by contacting it under aromatization conditions with a catalyst according to the invention. Mixtures of carbon monoxide and hydrogen suitable as feed for the abovementioned process may be prepared by steam gasification at high temperature of carbon-containing material. Examples of such materials are lignite, anthracite, coke, crude petroleum and fractions thereof, as well as oils produced from tar sand and from bituminous shale. During the steam gasification the feed, in a finely dispersed form, is converted with steam and oxygen or air enriched with oxygen, if desired, into a gas mixture comprising, inter alia, hydrogen, carbon monoxide, carbon dioxide, nitrogen and water. The steam gasification is preferably carried out at a temperature between 1000° and 2000° C. and a pressure between 10 and 50 bar. In order to enable the removal of impurities such as ash, carbonaceous material and hydrogen sulphide from the gas obtained in the steam gasification, which gas has a temperature of more than 1000° C., this gas must first be cooled to a temperature between 100° and 200° C. This cooling may be very suitably effected in a boiler in which steam is generated by means of the waste heat. The cooled gas may be freed from practically all solid matter by washing with water. After this wash, in which the temperature of the gas has fallen to 20°–80° C., the gas is further purified by removal of hydrogen sulphide and carbon dioxide. This may be very suitably effected by means of the ADIP process or the SULFINOL process. For the preparation of aromatic hydrocarbon mixtures starting from a mixture of carbon monoxide and hydrogen, gas mixtures are preferred having a $H_2/CO$ molar ratio between 1.0 and 3.0 and in particular between 1.5 and 2.5. If the available mixture of hydrogen and carbon monoxide does not have the required molar ratio, this may be adjusted by adding hydrogen or carbon monoxide. An increase of the hydrogen content of the mixture at the cost of the carbon monoxide content may also be very suitably effected by submitting the mixture to the well-known water gas shift reaction. The conversion of a mixture of carbon monoxide and hydrogen into an aromatic hydrocarbon mixture according to the invention is preferably carried out at a temperature of 200°–500° C. and in particular of 300°–450° C., a pressure of 1–150 bar and in particular of 5–100 bar and a space velocity of 50–5000 and in particular of 300–3000 Nl gas/l catalyst/hour.

Catalysts with activity for the conversion of $H_2/CO$ mixture to substantially oxygen-containing hydrocarbon preferably contain one or more of the metals zinc, chromium and copper. Preference is further given to catalysts in which at least a combination of two of these metals occurs, e.g. the combinations zinc-copper, zinc-chromium or zinc-copper-chromium. In particular preferred is a catalyst comprising the combination zinc-chromium. If a catalyst is employed which is capable of converting a $H_2/CO$ mixture to substantially oxygen-containing hydrocarbons, preference is given to a catalyst which can convert the $H_2/CO$ mixture to substantially methanol, the above-mentioned metal combinations are very suitable. If desired, said metal combinations may be applied on a carrier material. By introduction of an acid function into these catalysts, e.g. by applying the metal combination on an acid carrier, it can be attained that the $H_2/CO$ mixture is converted not only to methanol but also for a considerable part to dimethyl ether.

Catalysts with activity for the conversion of a $H_2/CO$ mixture to substantially hydrocarbons are well-known as Fischer-Tropsch catalysts. As a rule these catalysts contain one or more of the metals of the iron group or ruthenium together with one or more promoters to increase the activity and/or selectivity and sometimes a carrier material such as kieselguhr. They may be prepared by precipitation, by melting or by impregnation. If the aromatization process according to the invention starting from a $H_2/CO$ mixture, use is made of a Fischer-Tropsch catalyst, preference is given to an iron or cobalt catalyst, in particular such as catalyst which has been prepared by impregnation. Very suitable Fischer-Tropsch catalysts for application in the aromatization process starting from a $H_2/CO$ mixture are the Fischer-Tropsch catalysts described in Netherlands patent application No. 7612460. In the aromatization process according to the invention starting from a $H_2/CO$ mixture use can also be made of either a single catalyst having activity for the conversion of a $H_2/CO$ mixture to a mixture comprising hydrocarbons as well as oxygen-containing hydrocarbons in comparable amounts or two catalysts of which one shows catalytic activity for the conversion of a $H_2/CO$ mixture to substantially hydrocarbons whereas the other shows catalytic activity for the conversion of a $H_2/CO$ mixture to substantially oxygen-containing hydrocarbons.

The most important application of the catalysts according to the invention lies in the field of the preparation of synthetic gasoline from coal by (a) steam gasification of the coal, (b) conversion of the $H_2/CO$ mixture thus obtained into a mixture substantially consisting of hydrocarbons, preferably over a Fischer-Tropsch catalyst, or into a mixture substantially consisting of oxygen-containing hydrocarbons, preferably over a methanol synthesis catalyst, and (c) conversion of the product obtained in reaction (b) into an aromatic gasoline over a catalyst according to the invention.

The aromatization process according to the invention is further eminently suitable for the selective preparation of p-xylene from isobutene. For, it has been found that the catalysts according to the invention have the surprising property of converting isobutene into a highly aromatic product, the $C_8$—aromatics fraction of which has a much higher p-xylene content than $C_8$—aromatics fractions obtained in the conventional processes for the preparation of p-xylene. A similar phenomenon is observed in the use of the catalysts according to the invention in the preparation of p-xylene by methylation of toluene. Here too a product is obtained of which the $C_8$-aromatics fraction has a surprisingly high p-xylene content. Very suitable catalysts for the preparation of p-xylene by aromatization of lower hydrocarbons are the following catalysts according to the invention:

(a) a catalyst containing at least 0.2%w boron;
(b) a catalyst containing at least 0.5%w magnesium;
(c) a catalyst containing an oxide of antimony.

The preparation of p-xylene may also very suitably be carried out by contacting $C_1$–$C_4$ alcohols, ethers derived therefrom or mixtures thereof under aromatization conditions with a catalyst according to the invention comprising a silicate with a crystal size of at least 1 micron. A very suitable feed for this purpose is methanol.

In addition to their use as catalysts or catalyst carriers the silicates according to the invention are also suitable for many other applications, such as for use as adsorbing and extracting agents, as drying agents, as ion exchangers and as molecular sieves.

The invention will now be elucidated with reference to the following example.

EXAMPLE

Six silicates (1–6) were prepared as follows:

Silicate 1

A mixture of $Fe(NO_3)_3$, $SiO_2$, $NaNO_3$ and $[(C_3H_7)_4N]OH$ in water having the molar composition $Na_2O$. $4.5[(C_3H_7)_4N]_2O$. $Fe_2O_3$. 29.1 $SiO_2$. 468 $H_2O$ was heated for 48 hours in an autoclave at 150° C. under autogenous pressure. After the reaction mixture had cooled down the silicate formed was filtered off, washed with water till the pH of the wash water was about 8 and dried for two hours at 120 C. Silicate 1 thus prepared had the following chemical composition:

$0.67[(C_3H_7)_4N]_2O$. 0.23 $NaO$. $Fe_2O_3$. 30 $SiO_2$. 9 $H_2O$.

Silicate 2

This silicate was prepared in substantially the same manner as silicate 1, the difference being that in the present case the starting material was an aqueous mixture having the molar composition:

Na$_2$O. 4.5[(C$_3$H$_7$)$_4$N]$_2$O. 0.5 Fe$_2$O$_3$. 29.1 SiO$_2$. 468 H$_2$O. Silicate 2 thus prepared had the following chemical composition:

0.80[(C$_3$H$_7$)$_4$N]$_2$O. 030 Na$_2$O. Fe$_2$O$_3$. 45 SiO$_2$. 13 H$_2$O.

Silicate 3

This silicate was prepared in substantially the same manner as silicate 1, the difference being that in the present case the starting material was an aqueous mixture which, in addition to Fe(NO$_3$)$_3$, contained Al(NO$_3$)$_3$ and had the following molar composition:

Na$_2$O. 4.5[(C$_3$H$_7$)$_4$N]$_2$O. 0.33 Al$_2$O$_3$. 0.67 Fe$_2$O$_3$. 29.1 SiO$_2$. 428 H$_2$O.

Silicate 3 thus prepared had the following chemical composition:

0.55[(C$_3$H$_7$)$_4$N]$_2$O. 0.45 Na$_2$O. 0.67 Fe$_2$O$_3$. 0.33 Al$_2$O$_3$. 30 SiO$_2$. 10 H$_2$O.

Silicate 4

This silicate was prepared in substantially the same manner as silicate 3, the difference being that in the present case the starting material was an aqueous mixture having the following molar composition:

Na$_2$O. 4.5[(C$_3$H$_7$)$_4$N]$_2$O. 0.5 Al$_2$O$_3$. 0.5 Fe$_2$O$_3$. 29.1 SiO$_2$. 428 H$_2$O. Silicate 4 thus prepared had the following chemical compositions:

0.86[(C$_3$H$_7$)$_4$N]$_2$O. 0.3 Na$_2$O. 0.55 Fe$_2$O$_3$. 0.45 Al$_2$O$_3$. 32 SiO$_2$. 8 H$_2$O.

Silicate 5

This silicate was prepared in substantially the same manner as silicate 1, the difference being that in the present case the starting material was an aqueous mixture containing Al(NO$_3$)$_3$ instead of Fe(NO$_3$)$_3$ and having the following molar composition:

Na$_2$O. 4.5[(C$_3$H$_7$)$_4$N]$_2$O. Al$_2$O$_3$. 29.1 SiO$_2$. 410 H$_2$O.
The silicate thus prepared had the following chemical composition:

0.4[(C$_3$H$_7$)$_4$N]$_2$O. 0.2 Na$_2$O. Al$_2$O$_3$. 21.6 SiO$_2$. 7 H$_2$O.

Silicate 6

This silicate was prepared in substantially the same manner as silicate 1, the difference being that in the present case the starting material was an aqueous mixture containing no Fe(NO$_3$)$_3$ and having the following molar composition:

Na$_2$O. 4.5[(C$_3$H$_7$)$_4$N]$_2$O. 29.1 SiO$_2$. 430 H$_2$O.

Silicates 1-6 prepared as described above all had an X-ray powder diffraction pattern substantially in line with Table B. The thermal stabilities of silicates 1-6, and the quantities of water they adsorb at 25° C. after dehydration at 400° C. in vacuum, and saturated water vapor pressure are given in Table C.

TABLE C

| Silica No. | Thermally stable up to temperatures above, °C. | Adsorbed water, %w |
|---|---|---|
| 1 | 1000 | 8.0 |
| 2 | 950 | 7.5 |
| 3 | 1050 | 8.2 |
| 4 | 1000 | 7.8 |
| 5 | 1000 | 6.0 |
| 6 | 800 | 6.1 |

Silicates 7-12

With silicates 1-6 as the starting materials silicates 7-12, respectively, were prepared by successively calcining silicates 1-6 for four hours at 500° C., boiling with 1.0 molar NH$_4$NO$_3$-solution, washing with water, boiling again with 1.0 molar NH$_4$NO$_3$-solution and washing, drying for two hours at 120° C. and calcining for four hours at 500° C.

Silicates 13-15

With silicates 1, 3 and 6 as the starting materials silicates 13-15, respectively, were prepared by successively calcining silicates 1, 3 and 6 for four hours at 500° C., boiling for six hours with 0.5 molar K$_2$CO$_3$-solution, washing with water, drying for two hours at 120° C. and calcining for four hours at 500° C. The silicates thus prepared had the following overall composition, expressed in moles of the oxides.

Silicate 13

0.89 K$_2$O. 0.05 Na$_2$O. Fe$_2$O$_3$. 30 SiO$_2$.

Silicate 14

0.94 K$_2$O. 0.08 Na$_2$O. 0.67 Fe$_2$O$_3$. 0.33 Al$_2$O$_3$. 30 SiO$_2$.

Silicate 15

0.005 K$_2$O. SiO$_2$.

Of the silicates 1-15 described above only silicates 1-4, 7-10, 13 and 14 are silicates according to the invention. Silicates 5, 6, 11, 12 and 15, which contain no iron, fall outside the scope of the invention and have been included for comparison.

On comparison of the overall compositions of silicates 13 and 14 with those of silicates 1 and 3, respectively, it is found that in the silicates according to the invention iron is present in a non-exchangeable form. It is further found that in the silicates according to the invention the negative electrovalencies of iron and/or aluminum are offset by exchangeable cations in such a way that in the present case for each iron and/or aluminum atom substantially one monovalent cation is present. The overall composition of zeolite 15 demonstrates that in the absence of iron and aluminum atoms in the silicate there is no question of exchangeable cations.

Preparation of p-xylene from isobutene

Silicates 7-9 and 11 and 12 were tested as catalysts in the preparation of p-xylene from isobutene. To this end isobutene was passed over a fixed bed of these silicates at atmospheric pressure, a temperature of 400° C. and a space velocity of 4 kg.kg$^{-1}$.h$^{-1}$. The results of these experiments are given in Table D.

TABLE D

| Exp. No. | Silicate No. | Yield of liquid reaction product, %w | Proportion of C$_6$-C$_9$ aromatic fraction in the liquid reaction product, %w | Proportion of C$_8$ aromatic fraction in the C$_6$-C$_9$ aromatic fraction, %w | Proportion of p-xylene in C$_8$-aromatic fraction, %w |
|---|---|---|---|---|---|
| 1 | 7 | 65 | 37.5 | 35 | 48.5 |
| 2 | 8 | 66 | 32 | 39 | 90 |
| 3 | 9 | 74 | 26 | 45 | 58 |
| 4 | 11 | 55 | 39 | 45 | 22 |
| 5 | 12 | 45 | 5 | 30 | 25 |

The results given in Table D clearly demonstrate the excellent suitability of the iron-containing silicates according to the invention as catalysts for the selective preparation of p-xylene from isobutene (experiments 1-3) in comparison with related silicates containing no iron (experiments 4 and 5).

Preparation of aromatics from methanol (experiment 6)

Silicate 8 was tested as a catalyst in the preparation of aromatics from methanol. To this end methanol was passed over a fixed bed of this silicate at a pressure of 5 bar, a temperature of 350° C. and a space velocity of 1 kg.kg$^{-1}$.h$^{-1}$. With 100 pbw methanol as the starting material 28.7 pbw of a mixture of liquid oxgen-free organic compound were thus obtained. The average carbon number of the compounds in the mixture was 9.5. The mixture comprised 59.6%w $C_6^+$ aromatics, distributed as follows over the various compounds.

0.2%w benzene;
2.8%w toluene;
2.4%w p-xylene;
2.4%w m-xylene;
4.5%w o-xylene;
15.0%w $C_9$-aromatics and
32.2%w $C_{10hu +}$ aromatics.

Preparation of an aromatic gasoline from n-hexadecan (experiment 7)

Silicate 9 was treated as a catalyst in the preparation of an aromatic gasoline from n-hexadecane. To this end n-hexadecane was passed over a fixed bed of this silicate at a pressure of 5 bar, a temperature of 375° C. and a space velocity of 1 1.1$^{-1}$.h$^{-1}$. The feed was completely converted into a product having the following composition:

|  | %w |
|---|---|
| $C_1$ | 0.0 |
| $C_2$ | 0.2 |
| $C_3$ | 5.9 |
| $C_4$ | 21.7 |
| $C_5$-$C_{12}$ | 68.0 |
| $C_{13}$-$C_{19}$ | 5.2 |

This liquid product contained 45% w aromatics.

EXAMPLE II

Ten silicates (16-25) were prepared as follows.

Silicates 16-18

Silicate 16 was prepared in substantially the same manner as silicate 1, the difference being that in the present case the starting mixture was an aqueous mixture having the molar composition:

0.8[($C_3H_7$)$_4$N]$_2$O.0.3 Na$_2$O.Fe$_2$O$_3$.200 SiO$_2$.55 H$_2$O.

From silicate 16, a silicate 17 was prepared in the same way that silicates 7-12 were prepared from silicates 1-16, respectively.

From silicate 16, silicate 18 was prepared by successively calcining silicate 16 for 4 hours at 500° C., boiling with 1.0 molar NaNO$_3$—solution, washing with water, boiling again with 1.0 molar NaNO$_3$—solution and washing, drying for 2 hours at 120° C. and calcining for 4 hours at 500° C. Silicate 18 thus prepared had the following chemical composition: Na$_2$O.Fe$_2$O$_3$.200 SiO$_2$.

Silicate 19

This silicate was prepared in substantially the same manner as silicate 1, the difference being that in the present case the starting mixture was an aqueous mixture which, in addition to Fe(NO$_3$)$_3$, containing Ga(NO$_3$)$_3$ and had the following molar composition:

Na$_2$O.1.5[(C$_3$H$_7$)$_4$N]$_2$O.0.125 Fe$_2$O$_3$.0.125 Ga$_2$O$_3$ 25.0 SiO$_2$.450 H$_2$O. Silicate 19 thus prepared had the following chemical composition:

0.75[(C$_3$H$_7$)$_4$N]$_2$O.0.28 Na$_2$O.0.51 Fe$_2$O$_3$.0.49 Ga$_2$O$_3$.100 SiO$_2$.23 H$_2$O.

Silicates 20 and 21

Silicate 20 was prepared in substantially the same manner as silicate 1, the difference being that in the present case the starting mixture was an aqueous mixture containing no NaNO$_3$ and had the following molar composition:

1.5[(C$_3$H$_7$)$_4$N]$_2$O.Fe$_2$O$_3$.205 SiO$_2$.50 H$_2$O.

From silicate 20, a silicate 21 was prepared by calcining for 4 hours at 500° C.

Silicates 22 and 23

A first mixture comprising 6.18 of n-butyl amine, 46.2 g waterglass (28% SiO$_2$; 8% Na$_2$O) and 56.2 g water was mixed with a second mixture comprising 1.3 g Fe$_2$(SO$_4$)$_3$.9 H$_2$O, 3.75 g H$_2$SO$_4$ and 77 g water. The mixture thus obtained was stirred for 2 hours at room temperature and thereafter heated for 48 hours, with stirring, in an autoclave at 150° C. under autogeneous pressure. After the reaction mixture had been cooled down the silicate formed was filtered off, washed with water till the pH of the wash water was about 8 and dried for 2 hours at 120° C. From the silicate 22 thus obtained a silicate 23 was prepared in the same way that silicates 7-12 were prepared from silicates 1-6, respectively. The silicate 23 thus obtained had the following chemical composition:

H$_2$O.Fe$_2$O$_3$.94 SiO$_2$.

Silicate 24

Silicate 24 was prepared in substantially the same manner as silicate 23, the difference being that in the present case the first mixture contained 8.4 g of piperidine instead of 6.18 g of n-butyl amine. The silicate 24 thus prepared had the following chemical composition:

H$_2$O.Fe$_2$O$_3$.90 SiO$_2$.

Silicate 25

This silicate was prepared in substantially the same manner as silicate 24, the difference being that in the present case the second mixture contained no Fe$_2$(SO$_4$)$_3$. Silicate 25 thus obtained was an amorphous product which did not adsorb water. This example demonstrates that the presence of iron plays an important role is the formation of a crystalline product.

Silicates 16, 19, 20 and 23 prepared as described above all had an X-ray powder diffraction pattern substantially in line with Table B. The thermal stabilities of silicates 16, 19, 20, 23 and 24 and the quantities of water which—after dehydration at 400° C. in vacuo—they adsorb at 25° C. and saturated water vapor pressure, are given in Table E.

TABLE E

| Silicate No. | Thermally stable up to temperatures above, °C. | Adsorbed water, %w |
|---|---|---|
| 16 | 900 | 7.0 |
| 19 | 900 | 7.2 |
| 20 | 900 | 7.0 |
| 23 | 950 | 7.0 |
| 24 | 700 | 4.5 |

Silicates 24 had an X-ray powder diffraction pattern (Radiation: Cu-Kα, wave length: 0.15418 nm) as given in Table F.

TABLE F

| $2\theta$ | Relative intensity (100. I/I) | Description of the reflection |
|---|---|---|
| 7.8 | 4 | NL |
| 9.3 | 100* | NL |
| 12.5 | 18 | SP |
| 12.7 | 24 | SP |
| 13.45 | 25 | SP |
| 15.3 | 9 | NL |
| 15.6 | 4 | NL |
| 17.9 | 20 | NL |
| 18.3 | 4 | NL |
| 18.6 | 3 | NL |
| 19.4 | 3 | NL |
| 20.95 | 9 | NL |
| 22.3 | 88 | SP |
| 22.45 | 46 | SP |
| 23.0 | 25 | SP |
| 23.5 | 52 | SP |
| 23.8 | 10 | SP |
| 24.2 | 33 | SP |
| 25.15 | 88 | SP |
| 25.6 | 88 | SP |
| 26.2 | 22 | SP |
| 26.7 | 26 | NL |
| 28.4 | 25 | SP |
| 29.1 | 16 | SP |
| 30.1 | 9 | NL |
| 30.4 | 5 | NL |
| 30.8 | 6 | NL |
| 31.2 | 4 | NL |
| 32.9 | 5 | NL |
| 33.8 | 8 | NL |
| 34.2 | 2 | NL |
| 34.6 | 3 | NL |
| 34.9 | 3 | NL |
| 36.1 | 7 | NL |
| 36.55 | 4 | NL |
| 37.1 | 5 | BD |
| 38.05 | 4 | BD |
| 38.8 | 3 | NL |
| 39.4 | 4 | NL |
| 39.7 | 3 | NL |

*$I_o$ = intensity of the strongest separated reflection occurring in the pattern.

The letters in Table F used to describe the reflections have the following meanings: SP=sharp; NL=normal; BD=broad; $\theta$=angle according to Bragg's law.

Of the silicates 16-25, silicate 25, which is an amorphous product, falls outside the scope of the invention and has been included in the patent application for comparison.

Preparation of an aromatic gasoline from n-hexadecane (experiment 8)

Silicate 17 was tested as a catalyst in the preparation of an aromatic gasoline from n-hexadecane. To this end n-hexadecane was passed over a fixed bed of this silicate at a pressure of 5 bar, a temperature of 375° C. and a space velocity of 1 1.1$^{-1}$.h$^{-1}$. The feed was completely converted into a product having the following composition:

| | %w |
|---|---|
| $C_1$ | 0.1 |
| $C_2$ | 0.6 |
| $C_3$ | 5.8 |
| $C_4$ | 17.4 |
| $C_5$-$C_{12}$ | 71.1 |
| $C_{13}$-$C_{19}$ | 4.5 |

The liquid product contained 40% w aromatics.

Preparations of p-xylene by methylation of toluene (experiment 9)

Silicate 17 was tested as a catalyst in the preparation of p-xylene by methylation of toluene. To this end a mixture of toluene and methanol in equimolar amounts was passed over a fixed bed of this silicate at a pressure of 5 bar, a temperature of 375° C. and a space velocity of 1 1.1$^{-1}$.h$^{-1}$.

The results of the experiment were as follows:
Conversion of toluene: 44%w
Conversion of methanol: 100%w
Selectivity to $C_8$-aromatics: 65%
Amount of p-xylene in the $C_8$-aromatics fraction: 80%

Separation of p-xylene from a mixture of p-xylene and m-xylene (experiment 10)

Silicate 18 was tested for the separation of p-xylene from a mixture of p-xylene and m-xylene. To this end a mixture of p-xylene and m-xylene in equimolar amounts was passed, in the vapor phase and diluted with nitrogen, over this silicate at a xylene partial pressure of 0.3 bar and a temperature of 80° C. After 4 hours the silicate was desorbed at 80° C. with toluene. GLC analysis of the toluene solution showed that p-xylene and m-xylene were present therein in a molar ration of 42:1.

Separation of p-xylene from a mixture of p-xylene and o-xylene (experiment 11)

Silicate 18 was tested for the separation of p-xylene from a mixture of p-xylene and o-xylene in the same way as described above for the separation of p-xylene from a mixture of p-xylene and m-xylene. GLC analysis of the toluene solution showed that p-xylene and o-xylene were present therein in a molar ratio of 36.5:1.

What is claimed is:

1. A process for the preparation of aromatic hydrocarbons which comprises
   contacting as feed at least one acyclic organic compound or a mixture of substantially acyclic organic compounds with shaped catalyst particles comprising from about 0-90% w of binder material and 10-100% w of crystalline silicates, which silicates are characterized in that:
   (a) they are thermally stable up to temperatures above 600° C.;
   (b) after dehydration in vacuum at 400° C. they are capable of absorbing more than 3% w water at 25° C. and saturated water vapor pressure; and
   (c) in the dehydrated form they have the following overall composition, in terms of moles of the oxides:

$(1.0 \pm 0.3)(R)_{2/n}O.[a\ Fe_2O_3.b\ Al_2O_3.c\ Ga_2O_3].y(d\ SiO_2.e\ GeO_2)$, where R=one or more monovalent or bivalent cations introduced during preparation of said silicates and selected from the group consisting of alkaline metals, alkaline earth metals and organic cations obtained from primary, secondary and tertiary alkylamines and quaternary ammonium compounds;

$a > 0.5$
$b \geq 0;$
$c \geq 0;$ $a + b + c = 1;$ $y = 10$ to $300$
$d \geq 0.1;$
$e \geq 0;$
$d + e = 1,$ n is the valency of R; and their X-ray diffraction patterns include, inter alia, the reflections given in Table A of this specification.

2. A process according to claim 1, wherein the acyclic organic compound is methanol.

3. A process according to claim 1, wherein the mixture of substantially acyclic organic compounds is a petroleum gasoline.

4. A process according to claim 1, wherein the mixture of substantially acyclic compounds is a product obtained in the hydrocarbon synthesis according to the Fischer-Tropsch Process.

5. A process according to claim 1 for the selective preparation of p-xylene wherein the acyclic organic compound is isobutene.

6. A hydrocarbon conversion process which comprises contacting a petroleum hydrocarbon fraction at an elevated temperature and pressure with shaped catalyst particles comprising from about 0–90% w of binder material and 10–100% w of crystalline silicates, which silicates are characterized in that;

(a) they are thermally stable up to temperatures above 600° C.;

(b) after dehydration in vacuum at 400° C. they are capable of absorbing more than 3% w water at 25° C. and saturated water vapor pressure; and (c) in the dehydrated form they have the following overall composition, in terms of moles of the oxides:

$(1.0 \pm 0.3)(R)_{2/n}O.[a\ Fe_2O_3.b\ Al_2O_3.c\ Ga_2O_3].y(d\ SiO_2.e\ GeO_2),$ where R = one or more monovalent or bivalent cations introduced during preparation of said silicates and selected from the group consisting of alkaline metals, alkaline earth metals and organic cations obtained from primary, secondary and tertiary alkylamines and quaternary ammonium compounds;

$a > 0.5$
$b \geq 0;$
$c \geq 0;$
$a + b + c = 1;$ $y = 10$ to $300$ $d \geq 0.1;$
$e \geq 0;$ $d + e = 1,$ n is the valency of R; and their X-ray diffraction patterns include, inter alia, the reflections given in Table A of this specification.

7. A process according to claim 6 for dewaxing of a gas oil distillate which comprises contacting said catalyst with a wax-containing gas oil distillate feed and separating a gas oil product having lower wax content than said feed.

8. A process according to claim 6 for the preparation of p-xylene which comprises contacting said catalyst with a hydrocarbon feed containing a mixture of isomeric $C_8$ aromatics and separating a hydrocarbon product having a p-xylene content higher than said hydrocarbon feed.

* * * * *